(12) United States Patent
Gajiwala (10) Patent No.: US 8,822,751 B2
(45) Date of Patent: Sep. 2, 2014

(54) ADHESIVE BANDAGE WITH BARRIER TEAR AWAY TABS

(76) Inventor: Kalpesh Jayantkumar Gajiwala, Mumbai (IN)

( * ) Notice: Subject to any disclaimer, the term of this patent is extended or adjusted under 35 U.S.C. 154(b) by 856 days.

(21) Appl. No.: 12/663,881

(22) PCT Filed: Jul. 4, 2008

(86) PCT No.: PCT/IN2008/000429
§ 371 (c)(1),
(2), (4) Date: Dec. 10, 2009

(87) PCT Pub. No.: WO2009/047789
PCT Pub. Date: Apr. 16, 2009

(65) Prior Publication Data
US 2010/0222731 A1    Sep. 2, 2010

(30) Foreign Application Priority Data

Jul. 18, 2007   (IN) .......................... 1385/MUM/2007

(51) Int. Cl.
*A61F 13/00*   (2006.01)
*A61F 15/00*   (2006.01)
*A61F 13/02*   (2006.01)

(52) U.S. Cl.
CPC ... *A61F 13/0203* (2013.01); *A61F 2013/00297* (2013.01); *A61F 2013/00289* (2013.01); *A61F 2013/00897* (2013.01); *A61F 2013/00817* (2013.01); *A61F 2013/008* (2013.01); *A61F 15/001* (2013.01)
USPC .............................................. 602/57; 602/54

(58) Field of Classification Search
USPC ..................... 602/54, 57, 41, 42, 52
See application file for complete search history.

(56) References Cited

U.S. PATENT DOCUMENTS

| 2,969,144 | A |   | 1/1961  | Zackheim |
| 4,176,664 | A | * | 12/1979 | Kalish ........................ 604/307 |
| 4,264,008 | A |   | 4/1981  | Kozlow |
| 4,265,234 | A |   | 5/1981  | Schaar |

(Continued)

OTHER PUBLICATIONS

International Search Report, Apr. 22, 2009 from International Phase of the instant application, PCT/IN2008/000429.

*Primary Examiner* — Patricia Bianco
*Assistant Examiner* — Keri J Nelson
(74) *Attorney, Agent, or Firm* — Fish & Tsang, LLP (57) ABSTRACT

The adhesive bandage consists of a support with one surface having pressure sensitive adhesive and a wound covering pad placed centrally on it, which are covered by two protective detachable tear away tabs. The tear away tab consists of a single layer over the adhesive surface of the support and becomes two layered over the pad region. The two layers are fused at the zone of fusion near the margin of the pad, but are otherwise free from each other. The layer close to the pad, called inner barrier layer, completely covers the pad area. The outer layer, also called grasping layer, partially covers the barrier layer and the pad, and is folded upon itself to give sufficient length. When the outer layer is grasped to pull apart the releasable tear away tabs the inner barrier layer prevents contact of the finger to the pad. As one pulls apart the tear away tabs the barrier layers unfold and prevent contact of the fingers with the wound and wound exudates, preventing cross contamination. The bandage is enclosed in an envelope with the free ends of uneven dimension to have free part of the surface of both leaves, which are easy to grasp and separate.

13 Claims, 10 Drawing Sheets

(56) References Cited

U.S. PATENT DOCUMENTS

| | | |
|---|---|---|
| 4,304,333 A | 12/1981 | Kozlow, Sr. |
| 4,418,822 A | 12/1983 | Dotta |
| 4,781,293 A | 11/1988 | Johns |
| 4,913,138 A | 4/1990 | Yoshida et al. |
| 5,052,381 A | 10/1991 | Gilbert et al. |
| 5,115,913 A | 5/1992 | Anhauser et al. |
| 5,188,124 A | 2/1993 | Feret |
| 5,275,284 A | 1/1994 | Onotsky |
| 5,333,753 A | 8/1994 | Etheredge |
| 5,397,297 A | 3/1995 | Hunter |
| 5,722,943 A | 3/1998 | Sessions |
| 5,792,092 A | 8/1998 | Turngren |
| 6,010,002 A | 1/2000 | Petterson |
| 6,124,522 A | 9/2000 | Schroeder |
| 6,140,549 A | 10/2000 | Pompei |
| 6,573,421 B1 | 6/2003 | Lemaire |
| 6,700,033 B1 | 3/2004 | Marcussen et al. |
| 6,719,137 B2 | 4/2004 | Dotta |
| 6,855,861 B2 | 2/2005 | Dotta |
| 6,923,320 B2 | 8/2005 | Grossman |
| 2006/0270959 A1 * | 11/2006 | Parker et al. .......... 602/57 |

* cited by examiner

ADHESIVE BANDAGE WITH BARRIER TEAR AWAY TABS

PRIOR APPLICATION

1385/MUM/2007; Patent Office Mumbai, India

REFERENCES SITED

US Patent Documents

| | | | |
|---|---|---|---|
| 2,969,144 | | | |
| 4,264,008 | | | |
| 4,265,234 | May 1981 | Schaar | 602/57, 206/441 |
| 4,304,333 | | | |
| 4,418,822 | December 1983 | Dotta | 206/441, 602/57 |
| 4,781,293 A | November 1988 | Johns | 206/441 |
| 4,913,138 | April 1990 | Yoshida | 602/57, 206/441 |
| 5,052,381 | October 1991 | Gilbert et al | 206/441, 128/155 |
| 5,115,913 A | May 1992 | Anhauser et al | 206/447; 206/440; 206/813 |
| 5,188,124 | February 1993 | Ferret | 128/889 |
| 5,275,284 | January 1994 | Onotsky | |
| 5,333,753 | | | |
| 5,397,297 | March 1995 | Hunter | |
| 5,722,943 A | March 1998 | Session | 602/57, 602/54, 206/440, 206/441 |
| 5,792,092 A | August 1998 | turngren | 602/57, 602/58, 602/900, 206/441 |
| 6,010,002 A | January 2000 | patterson | 206/440, 206/441 |
| 6,124,522 A | September 2000 | Scroeder | 602/57, 602/41, 602/43, 602/54, 206/440, 206/441 |
| 6,140,549 A | October 2000 | Pompei, Jr | 602/57, 602/41, 602/43, 602/54, 206/440, 206/441 |
| 6,573,421 B1 | June 2003 | Lemeire | 602/57, 602/54, |
| 6,700,033 B2 | March 2004 | Marcussen | 602/57, 602/54, 206/440, 206/441 |
| 6,719,137 B2 | April 2004 | Dotta | 206/440, 206/441, 602/57 |
| 6,855,861 B2 | February 2005 | Dotta | 602/57, 602/54, 206/440, 206/441 |
| 6,923,320 B2 | August 2005 | Grossman | 206/440, 602/57, 206/441 |

INTRODUCTION

Any injury, whether surgical or otherwise, results in a wound, which requires to be covered with a protective dressing to prevent contamination of the wound with germs, and also to absorb the exudate. Adhesive bandages are readymade onsite quick fixes and serve the purpose. Most adhesive bandages have a flat support with two surfaces, one which is non-adhesive and another which is an adhesive surface with a pressure sensitive adhesive on it and a protective and absorptive sterile pad situated mostly in the center, which is covered by pull away or tear away tabs also called removable or release liners. The entire assembly is put in an appropriate envelope, which is then sealed and sterilized to be dispensed and used later.

During application the tear away tabs are removed and the sterile pad is placed in contact with the wound. Most often while removing these tear away tabs however, one's finger or thumb comes in contact with the protective pad, which then becomes contaminated. Not only this, but while applying the bandage the applicant's finger and thumb can often come in direct contact with the wound. This causes two way contamination and possible transfer of infection, one, from the applicant's hand to the wound, and the other from the wound exudates to the applicant's hand. This is important as most often the one applying the bandage is a different person from the one who has the wound. Thus there is always a fear that the wound exudates can transmit infection, particularly lethal or incurable diseases like AIDS, Hepatitis etc., if there are any punctures, cracks, cuts, or wounds in the finger or thumb of the one applying the bandage. A few designs of adhesive bandages exist which attempt to prevent or minimize the contamination of the protective pad.

Here is a new design for an adhesive bandage that not only prevents the contact of the applicant's finger or thumb with the protective pad but also isolates them from the exuding wound thus preventing cross contamination. This ensures that the purpose of the sterile adhesive bandage is aptly served by maintaining the sterility of the bandage and the environment till the application of the bandage is complete. It protects both the applicant (one applying the bandage) and the injured. The design is also simple, cost effective and makes application of the bandage easy, as it does not substantially change the way people use conventional adhesive bandages like Band-Aid™.

Another problem, which is often encountered while applying an adhesive bandage, is the sticking together of the two leaves of the outer envelope, which have to be pulled apart to split open the envelope. Here an idea of design is described where one can easily grasp the two leaves of the envelope and separate them.

PRIOR ART AND BACKGROUND

There are several versions of adhesive bandages that have been described in prior art, since the time Earle Dickson invented his famous ready to use adhesive bandage, now popular as Band-Aid™. Most of the commonly available adhesive bandages have a protective layer covering the adhesive support and the pad. Some of these are invented with the aim of preventing contamination of the protective pad. In U.S. Pat. No. 5,397,297 to Hunter, Mar. 14, 1995, there are two tear away tabs of uneven length folded upon themselves. While removing these asymmetrical tear away tabs, the uneven distribution of pulling forces, leads to the protective pad being exposed to the applicant's fingers, as pointed out in U.S. Pat. No. 6,573,421 to Serge Lemaire, Jun. 3, 2003. The latter patent also has the aim of protecting the pad with one tear away tab completely folded and covering the pad, while another covering the first tab over the entire surface. In this version one has to pull the tabs unevenly. There is a possibility that the uneven pull may lead to uneven application and therefore possible exposure of the wound. On the other hand if the inner tab is pulled first then the second tear away tab may get stuck to the opposite end adhesive surface, leading to manual peeling and contamination. Another example is U.S. Pat. No. 5,333,753 to Etheredge, where the mechanism is created to avoid the inadvertent contact of the finger to the pad by securing the release sheet to the outer sheet forming the envelope. When the envelope is opened by pulling apart the outer sheets the release sheet comes off the bandage, freeing the bandage. Here the starting point is at one end of the adhesive bandage and away from the pad, therefore application in a controlled and precise manner may not be possible. U.S. Pat. No. 6,124,522 to Mark Schroeder, describes a method of applying the bandage with a single hand and incorporates the design in anticipation of the need to the use of latex gloves to avoid the risk of exposure to blood.

OBJECTIVE OF THE INVENTION

The objective of the present invention is to provide a simple, cost effective and safe mechanism for isolating the protective sterile pad of an adhesive bandage from the applicant's finger by a barrier and at the same time to isolate the applicant's fingers away from the contaminated wound. The present invention maintains the sterile environment, and preserves the sterility of the protective pad till the application is completed, and also prevents cross contamination of the wound and the applicant's finger, thereby safeguarding the user and the applicant against possible contamination and transmission of disease. Since in the preferred version the tear away tabs are substantially symmetrical, the pull is evenly distributed and the application is well controlled and precise. Further, due to the simplicity of the design, multiple gains are achieved with hardly any cost addition to existing known adhesive bandages like Band Aid™ (Johnson & Johnson). There is also described a design for the edges of the pull apart leaves of the envelope, making it easy to grasp and separate them.

THE STATEMENT OF INVENTION

The invention relates to an adhesive bandage comprising of a flat support with an adhesive surface and a protective, sterile pad, both covered by tear away tabs. The tear away tab has a single layer over the adhesive aspect of the bandage and becomes two layered over the protective pad area, so that in cross section it appears 'y' shaped. The two barrier layers of the tear away tab alternate with their opposite member in such a way that the innermost layer of one lies over the protective tab, covered by the innermost layer of the opposite tear away tab, which is covered by the outer layers of both tear away tabs. The whole assembly is packaged in a sealed envelope in which the edges of the two leaves of the envelope are unevenly cut to avoid creating an exact match and both have part of the surface uncovered by the other This makes it easy for the user to separate the two leaves for opening the envelope. In a related version the same mechanism can be used for transparent or nontransparent film dressing with or without any absorbent or medicated pad or material.

BRIEF DESCRIPTIONS OF THE ACCOMPANYING DRAWINGS

One must emphasize that the designs and dimensions seen in the drawings are for the purpose of demonstration and in no way limiting.

DESCRIPTION OF THE INVENTION

Figure 1A:
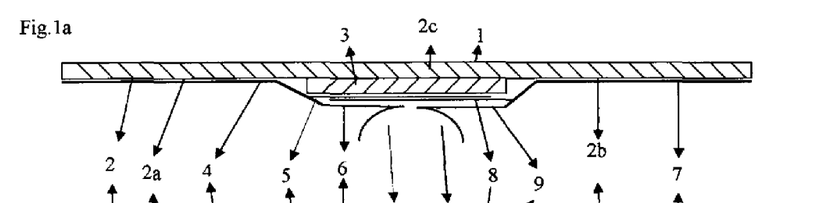
FIGS. 1a and 1b. The preferred embodiment in cross sectional and the top view respectively.
Figure 1B:
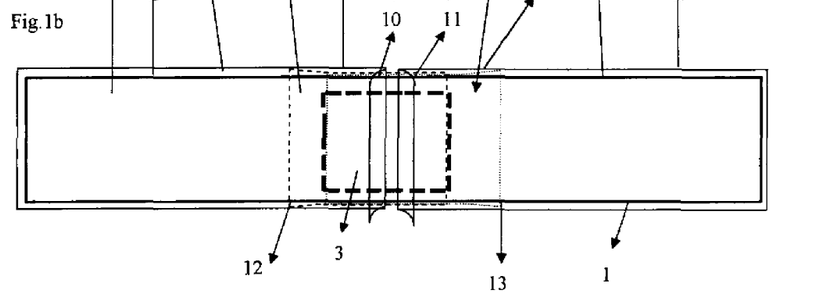
Figure 2:
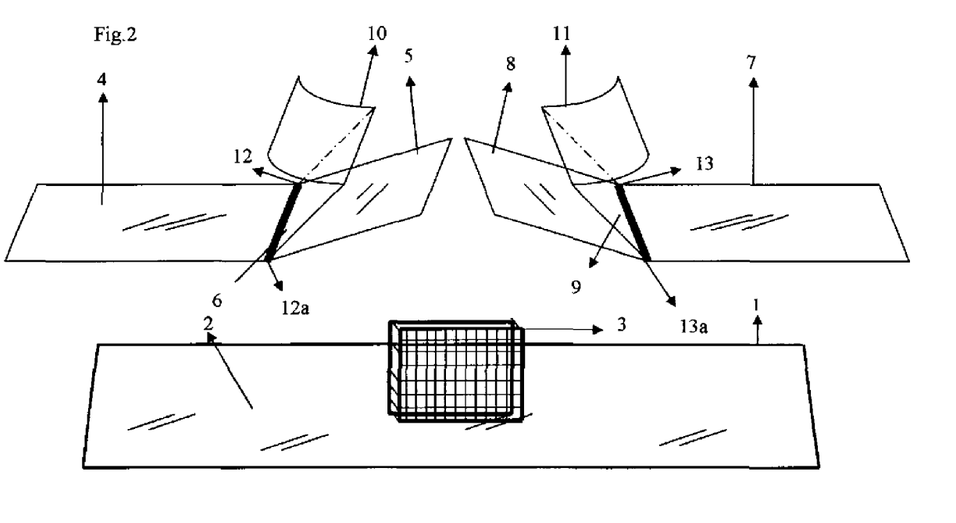
FIG. 2. Exploded perspective view of the preferred embodiment.

In the preferred embodiment, as shown in FIG. 1a, FIG. 1b and FIG. 2, the adhesive bandage comprises of a support 1, substantially rectangular, having one side or surface 2 adhesive with a protective sterile pad 3 which is preferably in the center of the adhesive side 2, thereby dividing the adhesive side into three parts 2a, 2b and 2c. Area 2c of the support over the pad may or may not be perforated. The adhesive support 2 itself may or may not be porous. Pad 3 is of such size that there is enough adhesive surface on all sides to seal the pad completely after application. One tear away barrier tab 4 covers adhesive surface 2a. It starts from one extremity of the support covering the surface 2b entirely towards pad 3. Close to the margin of pad 3 it becomes two layered denoted 5 and 6 and extends over the protective pad 3. The other tear away tab 7 covers adhesive surface 2b in a similar manner till near the margin of pad 3 where it becomes two layered denoted as 8 and 9 and extends over the protective pad area. Thus extensions 5 and 6 are continuous with adhesive tab 4 along the zone of fusion 12-12a and the extensions 8 and 9 are continuous with adhesive tab 7 along the zone of fusion 13-13a. The layers 5, 6, 8 and 9 are free and not adherent to each other or the pad. The arrangement of the two layered extensions of tab 4 and 7 is such that as seen in cross section FIG. 1 layers formed in the protective pad area are as follows; adhesive bandage support 1, protective pad 3, layer 5 inner barrier layer extension of tab 4, which preferably covers the entire surface of the pad 3, over that inner barrier layer 8 of tab 7 again covering extension 5 preferably almost completely, and over this outer grasping layer extensions 6 of tab 4 and 9 of tab 7, and they are arranged in such a way that they reach near about midline. Further to this preferably the ends of the extensions 6 and 9 are folded upon themselves as 10 and 11, substantially long enough to give a good grip. Though in FIG. 1 the outer grasping layers 6 and 9 are extending almost till the midline it may not necessarily be so and they may be shorter and folded back and the length of the folded aspect i.e. 10 and 11 be made much longer for easy grasping. There are also transparent and non transparent film dressings with or without pads, and the same mechanism can also be used with the film dressings to protect the wound, the covering area and the user from contamination. The space seen in FIG. 1, in cross section, between tear away tab 4 and adhesive surface 2a and likewise for 7 and 2b is for the purpose of clear visualization.

Figure 3:
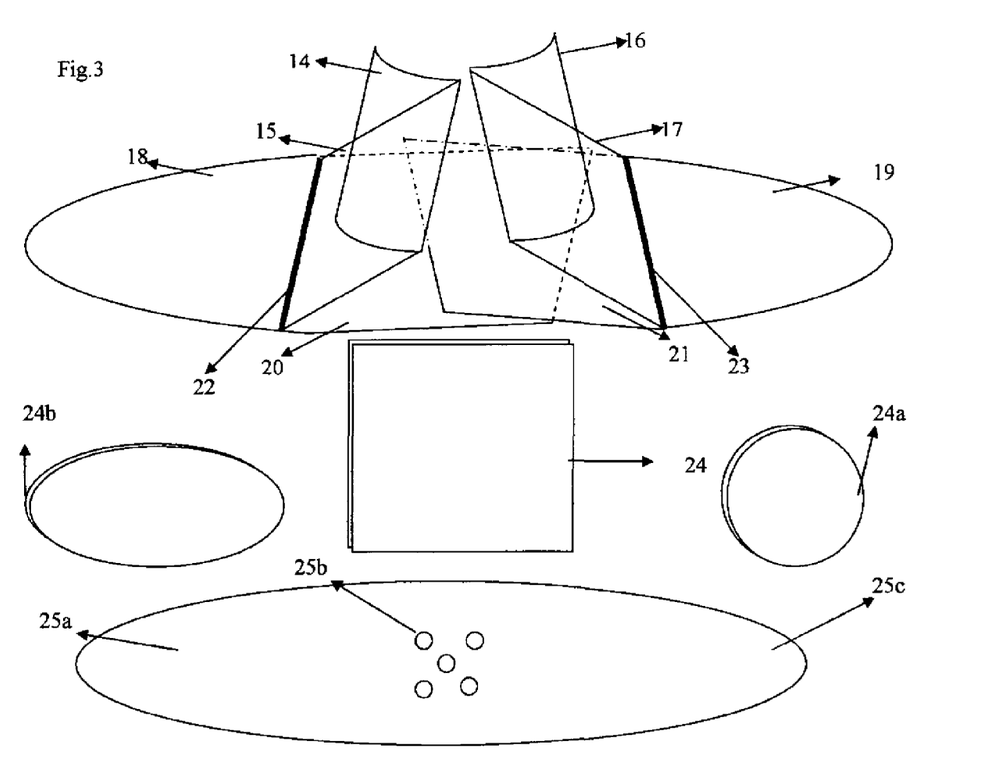
FIG. 3. Shows exploded perspective view of the similar arrangement for an oval shaped adhesive bandage along with the examples of variations in the design of the protective pad.

Though in the above embodiment the shape is substantially rectangular, this by no means restricts its application and one can choose any pattern with the similar principle of covering the protective pad. So one can create for example, round, oval, triangular, any polygonal shaped, or specific or non specific shaped, or irregular shaped support of the adhesive bandage with equal or unequal sides, and the description of all the possible different patterns for the adhesive support are beyond any one's scope. Thus one can create a design, which may be geometrical or irregular representing any shape. For example, in FIG. 3 a version is given with an oval shape where 18 and 19 are the tear away tabs covering the adhesive surface area 25a and 25b respectively. 15 and 17 are corresponding outer layer extension of tear away tabs 18 and 19 respectively. The outer layers 15 and 17 are layers to grasp and pull the tabs. 14 and 16 are folded extension of 15 and 17. 20 and 21 are inner barrier layer extensions of 18 and 19 respectively. 22 is the zone of fusion between outer grasping layer 15 and inner barrier layer 20, while 23 is the zone of fusion between the outer grasping layer 17 and the inner barrier layer 21. The strength at the zone of fusion is sufficient to keep the inner and outer layers together preventing it from breaking apart when the tear away tabs are pulled away, as inner barrier layers larger than protective pad may stick to the adhesive border around the pad. 24, 24a and 24b are various illustrative shapes of the pad. 25c is optionally perforated central adhesive zone over which the protective pad 24 rests. Optionally when the inner layers are larger than the pad, the adherent aspect of the border on either side may be thin, so that the adhesion if any formed with the inner layer of the tear away tab is thin and flimsy. Or optionally it may be so arranged that the border around the pad may be kept non-adherent. Or optionally the pad may extend from border to border to prevent the adhesion of the inner layer. The borders of the tear away tabs may optionally extend much beyond the borders of the support, but preferably extends at least up to the borders of the support.

Figure 4:
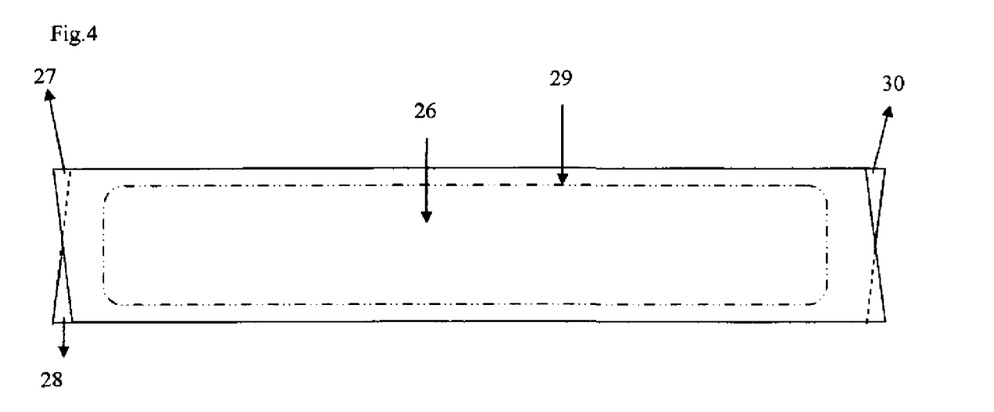
FIG. 4 Side view of the encasing envelope with uneven edges at the end.

FIG. 4 shows the outer envelope 26 is substantially like any outer envelope made up of two layers joined at 29 enclosing the adhesive bandage, with the difference that the edges of the two peel apart leaves 27 and 28 are obliquely or irregularly or unevenly cut so as to create uneven overlapping of the edges. Usually both the leaves are cut parallel and completely overlap each other causing them to adhere to each other and making it difficult to separate them. Here since surface 30 is free due to the uneven or oblique cut, it makes it easy to grasp and separate from its opposing member. This allows easy separation of the two leaves thereby improving the ease of opening the envelope.

Figure 5:
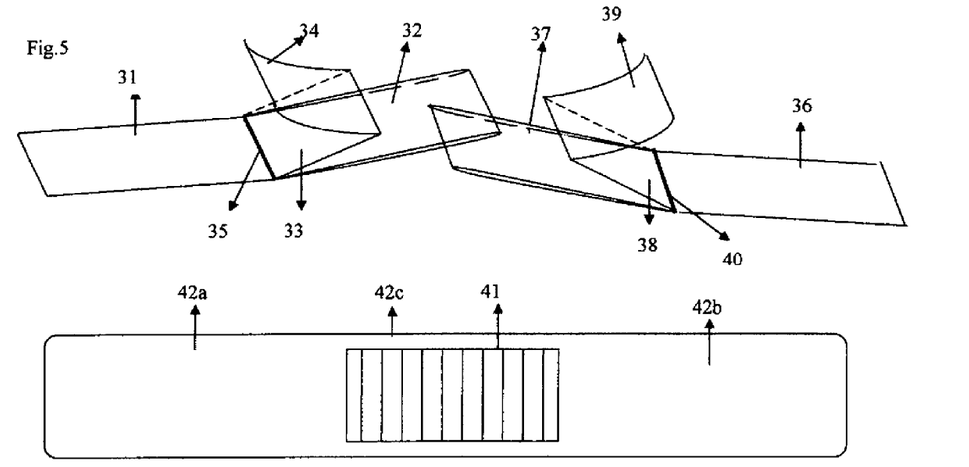
FIG. 5 Exploded view, illustration for the folded tear away tab made from the same strip.
Figure 6:
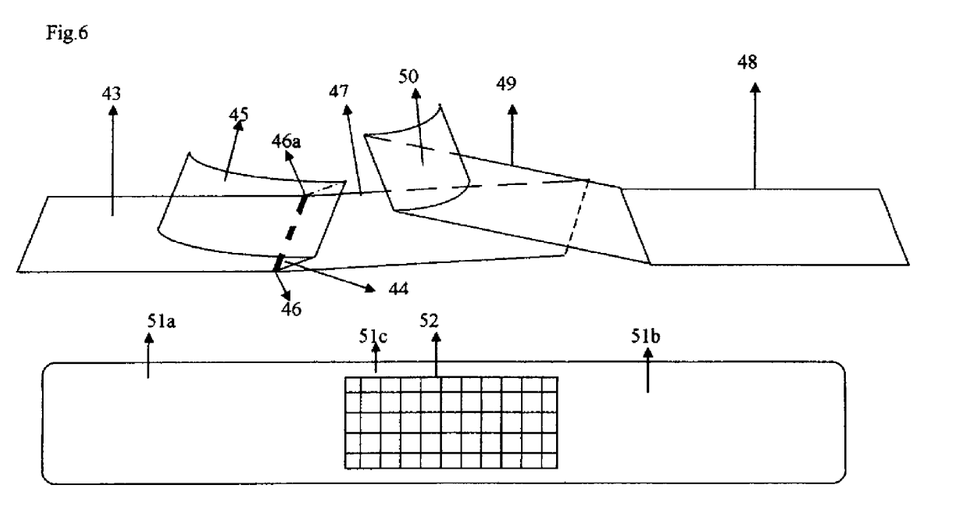
FIG. 6. Exploded view illustrates a variation with single inner barrier layer.

In another version of the preferred embodiment FIG. 5 shows a way of making a tear away tab from the same strip. Here tear away tab 31, which covers the adhesive area 42a, is folded upon itself to form a double layered inner barrier 32 that again turns to become the outer layer 33, fusing with 32 at zone 35. 34 is the backward extension of 33. The tear away tab 36, which covers the adhesive area 42b, is similarly folded upon itself to form the double layered inner barrier 37 that again turns to become the outer grasping layer 38 which fuses with 37 at zone 40. 39 is the backward extension of 38. 42c is the central adhesive zone over which a protective pad 41 rests. In another variation there is only one tear away tab with an inner protective barrier as shown in FIG. 6. Here the tear away tab 43 which covers adhesive surface area 51a has a two layer extension inner barrier layer 47 and a short outer layer 44 which is folded on itself as 45. Layers 44 and 47 are fused at zone 46-46a. Layer 47 completely covers the pad area 52. Another tear away tab 48, that covers the adhesive area 51b, extends as 49 over layer 47 to a large extent and folds itself as 50. Due to discrepancy in lengths of 44 and 49, the tear away tabs are unevenly distributed over the pad area. When pulled, the finger will not touch the underlying pad 52 due to barrier layer 47 covered by the long length of 49. A problem may arise in the application due to uneven pull and the lack of barrier for one finger, which may come in contact with the wound or the exudates leading to cross contamination.

Figure 7A:
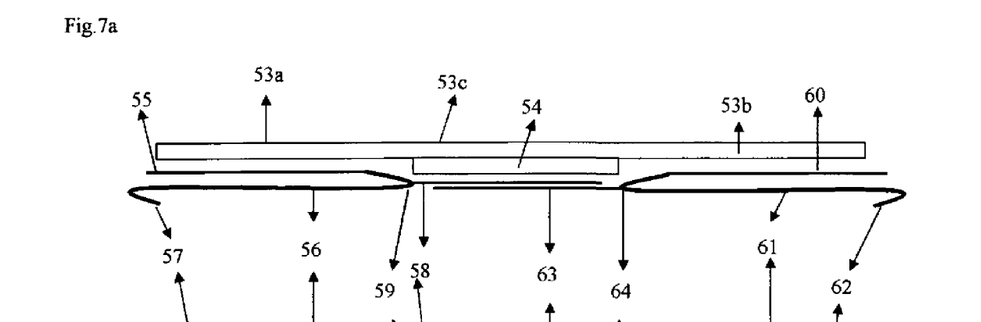
FIGS. 7a and 7b. A simple variation is illustrated in cross sectional view as well as a side by side view respectively of the support base and the tear away tabs, where the grasping layer is turned towards the extremity from the zone of fusion.
Figure 7B:
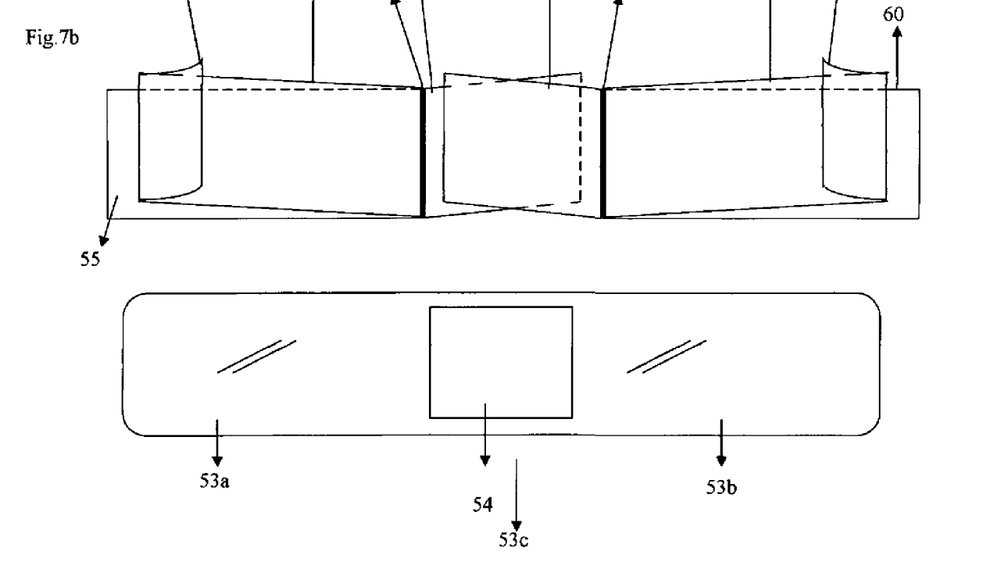

In another variation the grasping layer is turned away from the zone of fusion towards the extremity of the support as depicted in FIG. 7a and FIG. 7b. Here support is shown in three parts 53a, 53b and 53c. The protective pad 54 rests on the support at 53c. The tear away tab 55 starts from one extremity of the support completely covering the adhesive surface 53a. Near the margin it extends over the pad 54 as a barrier layer 58. The grasping layer 56 is fused with the tear away tab 55 at the zone of fusion 59. From the zone of fusion the layer 56 is turned away from the pad margin towards the extremity where it is folded back to extend as 57. Similarly the tear away tab 60 starts from the other extremity of the support completely covering the adhesive surface 53b. Near the margin it extends over the pad 54 as a barrier layer 63 completely or substantially covering the pad and the inner barrier layer 58. The grasping layer 61, which is fused with the tear away tab 60 at the zone of fusion 64, is turned away from the pad margin at the zone of fusion towards the extremity where it is folded back to extend as 62.

Figure 8:
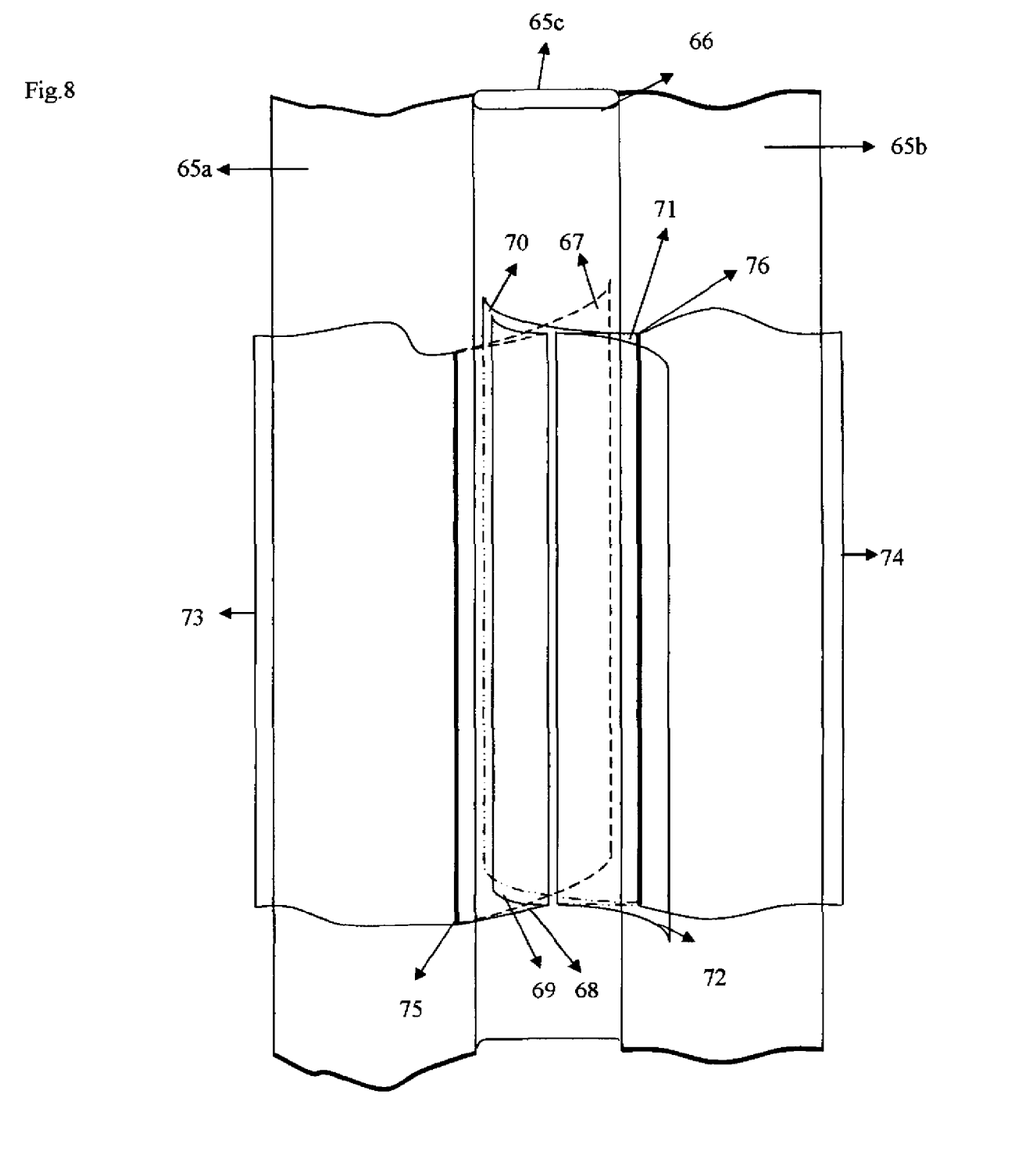
FIG. 8 shows how the preferred embodiment can be made into an elongated version, which can even be rolled.
Figure 9:
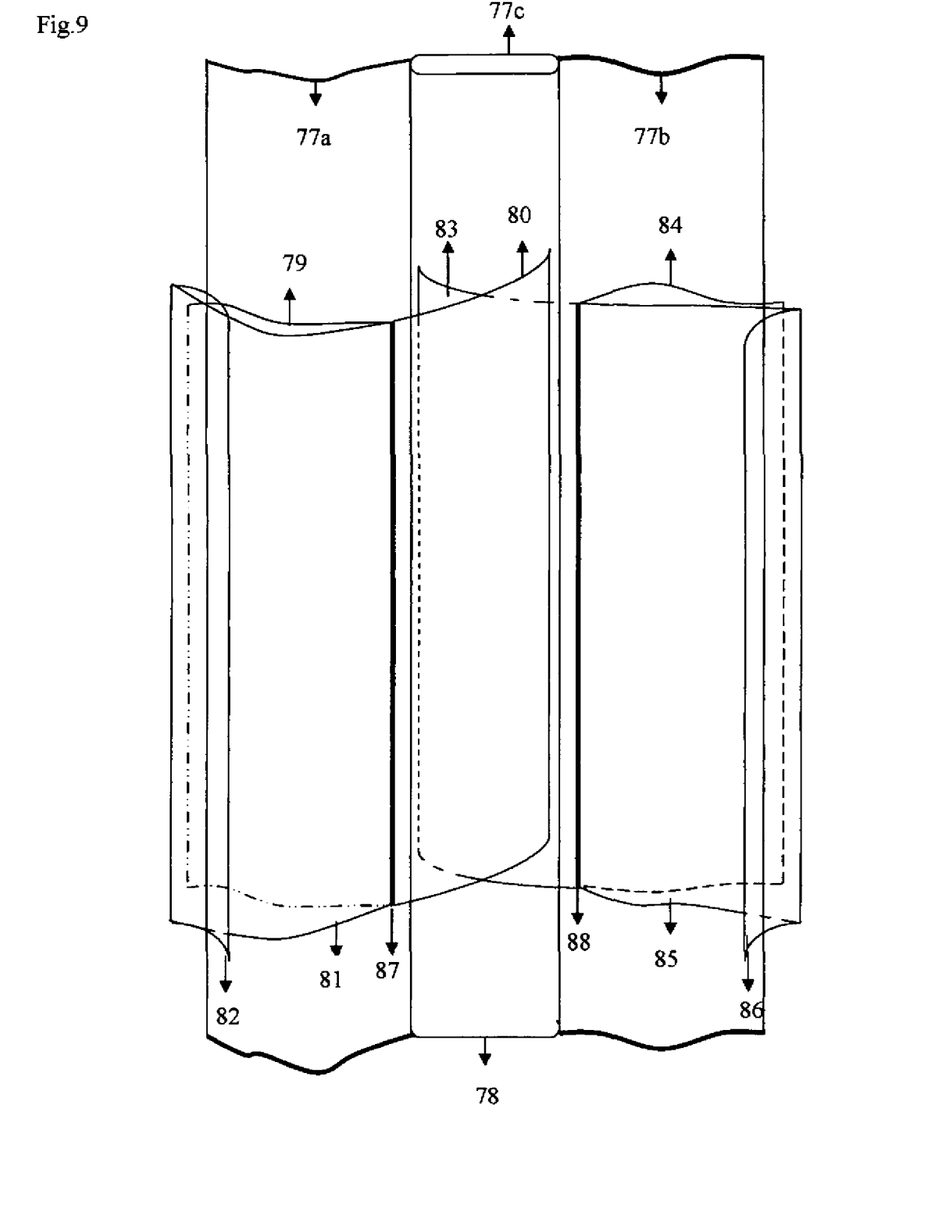
FIG. 9 shows how a variation of another embodiment, for example as shown in FIG. 7a and FIG. 7b, can be made into an elongated version and can possibly be rolled.

Another variation of the elongated version is shown in FIGS. 8 and 9. The FIG. 8 in cross section is the same as FIG. 1. An elongated support 65 is shown divided into three parts 65a, 65b and 65c. 66 is the elongated protective pad. 73 is elongated tear away tab which covers the entire adhesive surface 65a and extends over and preferably completely covers the pad 66 as the inner barrier layer 67 along its entire length. 68 is the outer grasping layer fused with 67 at the zone of fusion 75 and is folded back as extension 69. 74 is the elongated tear away tab which covers the entire adhesive surface 65b and extends over and preferably completely covers the pad 66 and the inner barrier layer 67 as barrier layer 70 along its entire length. 71 is the outer grasping layer fused with 70 at the zone of fusion 76 and is folded back as extension 72. In FIG. 8 the upper and lower limits of the support, the barrier layers, grasping layers and pad are only for the purpose of easy visualization and should not be considered limiting. The pad 66 may run along the entire length of the support 65, which can be then rolled and dispensed as such or may stop short leaving adhesive margins all around for a secure application.

FIG. 9 shows another variation of the elongated version which in cross section is same as FIG. 7. Here the support is shown in three parts 77a, 77b and 77c. The protective pad 78 rests on the support at 77c. The tear away tab 79 starts from one extremity of the support completely covering the adhesive surface 77a. Near the margin it extends over the pad 78 as a barrier layer 80. The grasping layer 81 is fused with the tear away tab 79 at the zone of fusion 87 From the zone of fusion the layer 81 is turned away from the pad margin towards the extremity where it is folded back to extend as 82. Similarly the tear away tab 84 starts from the other extremity of the support completely covering the adhesive surface 77b. Near the margin it extends over the pad 78 as a barrier layer 83 completely or substantially covering the pad and the inner barrier layer 80. The grasping layer 85, which is fused with the tear away tab 84 at the zone of fusion 88, is turned away from the pad margin at the zone of fusion towards the extremity, where it is folded back to extend as 86. The pad 78 may run along the entire length of the support 77, which can then be rolled and dispensed as such or may stop short leaving adhesive margins all around for a secure application.

Figure 10:
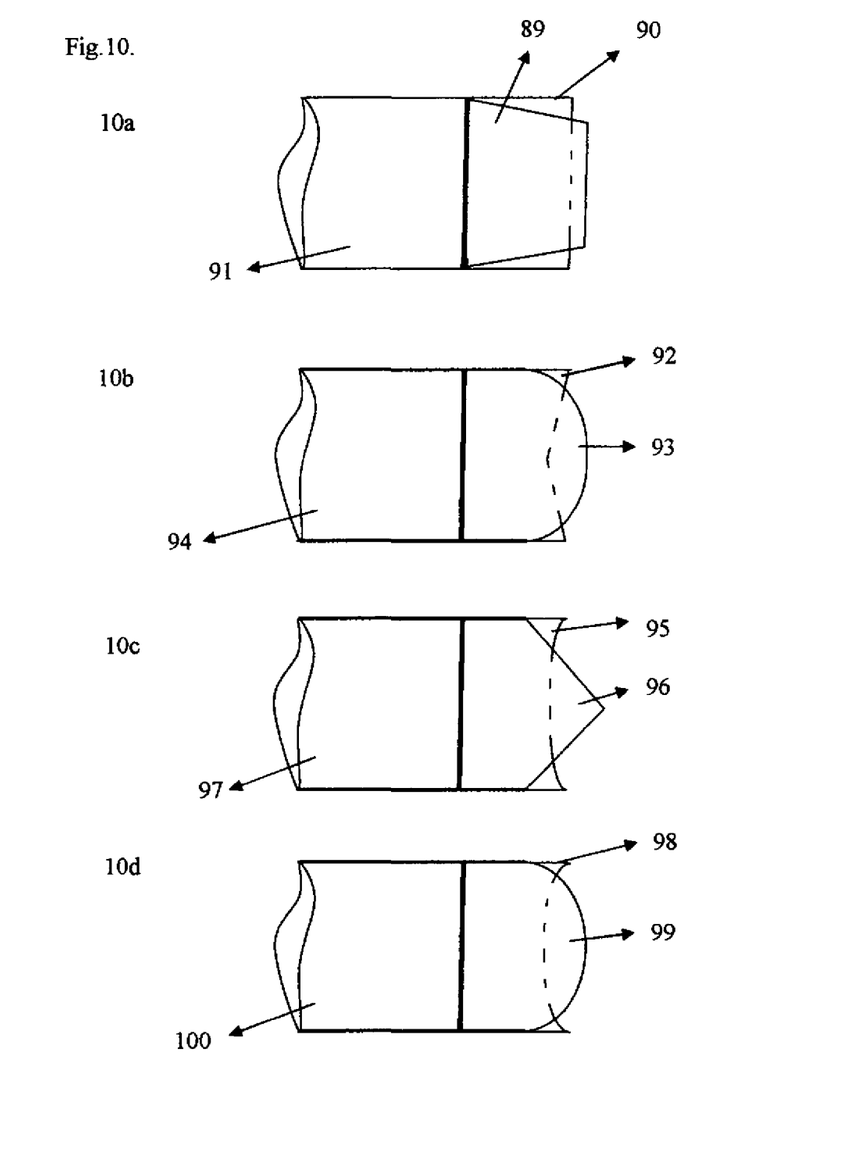
FIG. 10 shows some of the variations of the end of the encasing envelope for the adhesive bandage, where different arrangements are shown to demonstrate unequal lengths of two leaves of the envelope, so that it is easy to grasp and separate them. If the inner and outer surface are of different colours or shades then the better visualization simplifies grasping and separation.

In FIG. 10 some of the various possibilities of unevenly cut leaves of the envelope encasing the above adhesive bandage are shown. FIG. 10a shows the half cut envelope 91 and the uneven leaves 89 and 90. 90 is shorter but rectangular and 89 is trapezium but longer. Part of the surface of each leaf thereby remains uncovered by the other and therefore easy to grasp and separate. A similar principle is enunciated in the designs as seen in 10b, 10c and 10d. In FIG. 10b, 94 is the encasing envelope and 92 and 93 are the unevenly cut leaves. In FIG. 10c, 97 is the envelope and 95 and 96 are the unevenly cut leaves. In FIG. 10d, 100 is the envelope and 98 and 99 are the unevenly cut leaves. From the drawing it is apparent that infinite possibilities emerge keeping in mind the above principle.

Figure 11:
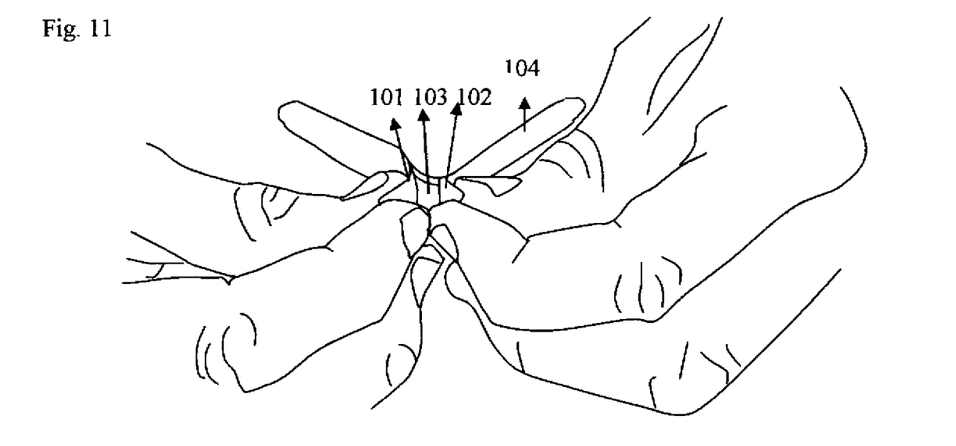
FIG. 11 shows the grasping of the commonly available adhesive bandage, where the single layer grip brings the fingers in contact with the sterile pad causing contamination. Also there is no barrier between the fingers and the wound to which the bandage would be applied.

Working of the Invention:

In commonly available adhesive bandages, there are no barrier layers between applicant's finger and the pad. One of the commonest design as shown in FIG. 11 depicts how when the tear away tabs or removable liners 101 and 102 are grasped, the protective sterile pad 103 based on adhesive support 104 comes in contact with the fingers of the applicant and thereby gets contaminated.

Figure 12:
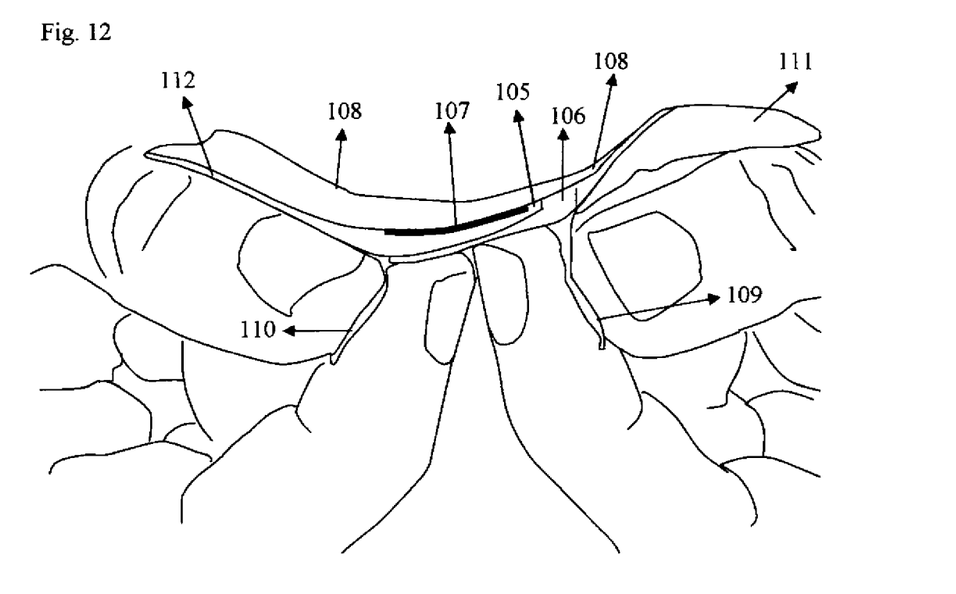
FIG. 12 demonstrates in a perspective view the grasping of the tear away, where the applicant's finger tips are prevented from touching the sterile pad 107 by the inner barrier layers 105 of tear away tab 112 and 106 of tear away tab 111.
Figure 13:
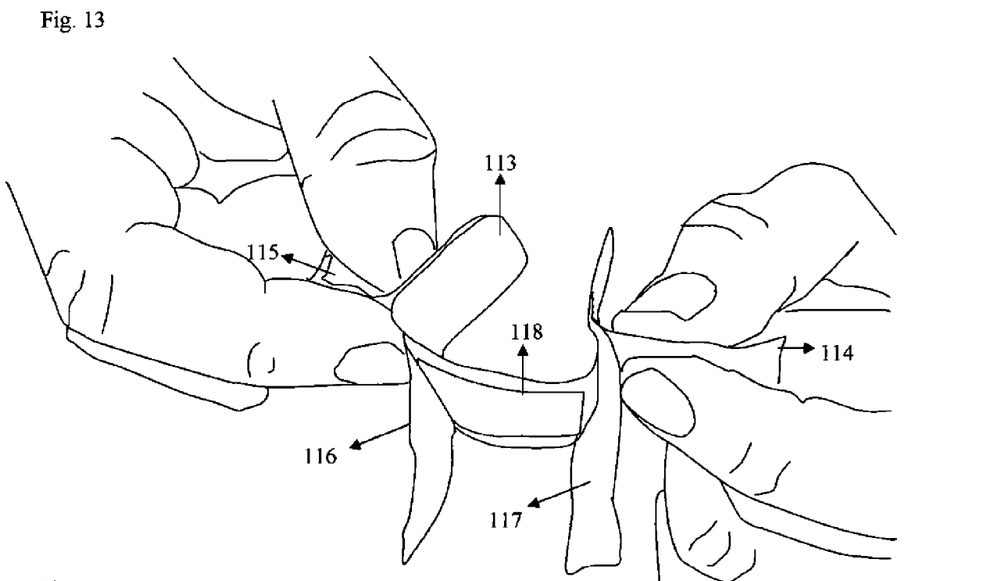
FIG. 13 shows the prevention of cross contamination of the wound and the applicant's finger by the barrier layers 116 and 117. As the tear away tabs are pulled apart the barrier layer unfolds.
Figure 14:
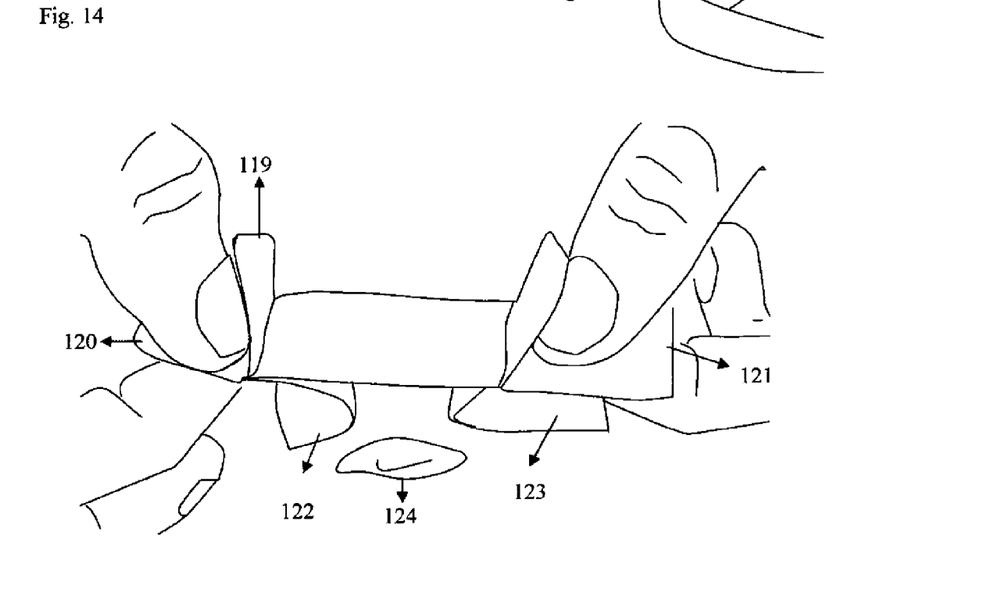
FIG. 14 shows that while the sterile pad is brought in contact with the wound the fingers are kept separated from the wound and the exudates by the barrier layers 120 and 121.
Figure 15:
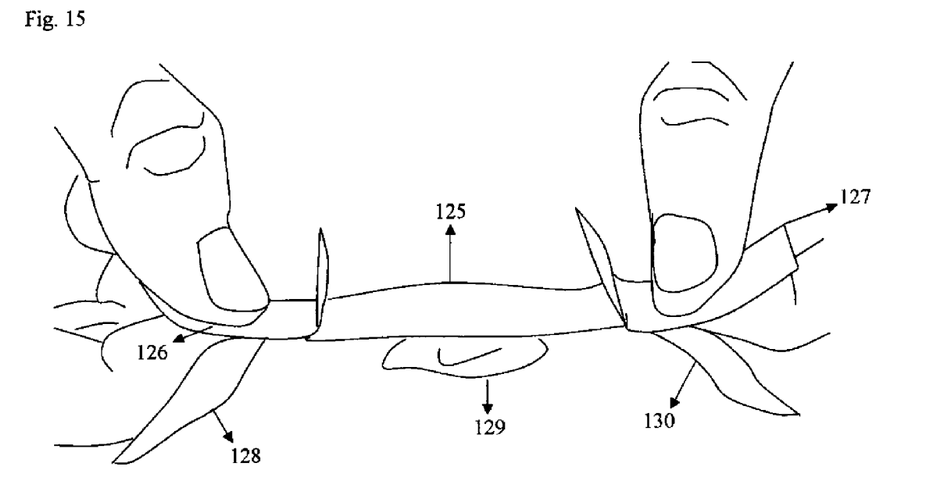
FIG. 15 shows how during the application of the barrier adhesive bandage the applicant's fingers continue to remain isolated from the pad as well as the wound and the skin, preventing cross contamination of the applicant's fingers as well as the wound and its environment.
Figure 16:
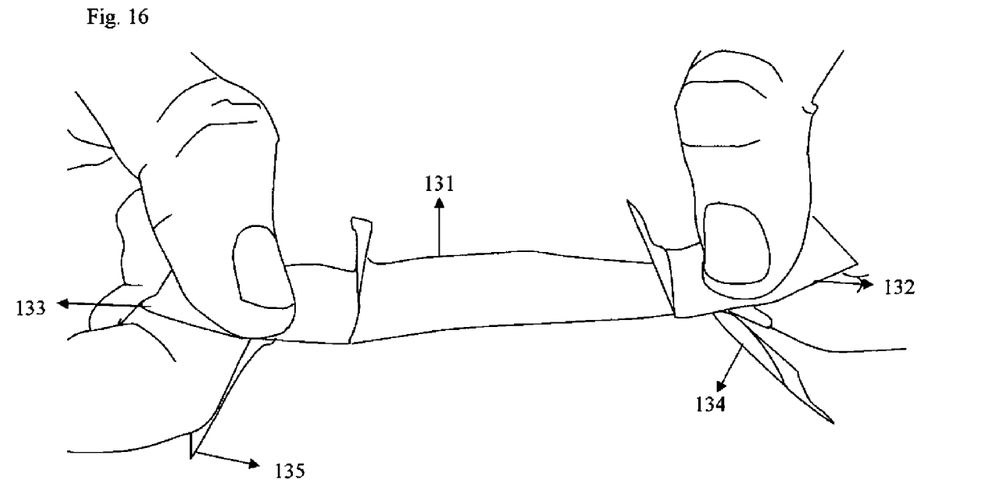
FIG. 16 shows the wound being sealed without any cross contamination of the sterile protective pad, the wound and the applicant's finger.

The working of the invention and the advantage it offers over the conventional adhesive bandage becomes evident when one sees FIGS. 12 to 16. First the affected area is properly cleansed. Then the leaves 98 and 99 of the encasing envelope 100 are grasped at the place where each leaf remains partly uncovered by the other as shown in FIG. 10d and therefore can be separated from each other easily. A little tug on this splits open the envelope 100. The adhesive bandage with the barrier tear away tabs is taken out. Now as seen in FIG. 12 the outer grasping layers 110 and 109 are grasped between finger and thumb of the respective hands in such a way that the finger tips lie in between the inner barrier layers 105 and 106, which cover the protective pad 107 on an adhesive support 108, and the outer layer 110 of the tear away tab 112 on one side, and the inner barrier layers 105 and 106 and the outer layer 109 of the tear away tab 111 on the other side. FIG. 13 shows that as the tear away tabs are pulled apart by holding the outer grasping layers 114 and 115 the inner barrier layers 116 and 117 unfold continuously isolating the applicant's fingers from the protective pad 118 based on the adhesive support 113. FIG. 14 further shows that as the applicant approaches the wound the barrier layers 122 and 123 now isolates the applicant's fingers from the wound 124 as well as the protective pad, as the tear away tabs held by the outer layers 120 and 121 are pulled apart. 119 is the adhesive bandage. In FIG. 15 one can see that as the adhesive bandage 125 is being applied to the wound 129, the fingers pulling the outer layers 126 and 127 are isolated by the barrier layers 128 and 130 from the wound 129, the pad as well as the surrounding skin, thereby preventing any cross contamination. FIG. 16 shows that the applicant's fingers grasping the outer barrier layers 132 and 133 remain isolated from the wound by the barrier layers 134 and 135 and only the sterile surface of the protective pad and the sterile adhesive surface of the adhesive bandage 131 comes in contact with the wound and the skin, as the application is completed. Thus barrier layers of the adhesive bandage prevent cross contamination between the applicant or the handler, the sterile protective pad and the wound. The other advantage is that it is used in a symmetrical manner and therefore can be applied with uniformity, in a controlled manner, with ease of use, more so if the two layers, the inner barrier and the outer grasping layers, are of different colours for the purpose of easy identification. From the above description it is also obvious that the design is simple and therefore easy to manufacture without much additional cost to currently available brands like Band Aid™, Handyplast etc.

By way of recapitulation, one can see from the foregoing descriptions and drawings that the present invention i.e. the adhesive bandage with a protective barrier layer and the encasing package provides significant advantages over conventional adhesive bandages in use. The main purpose of an adhesive bandage is to cover a wound in a sterile manner. The present invention ensures that the sterility of the protective pad is maintained till the wound is completely covered. It further prevents contact between applicant's fingers and the wound, and thereby prevents two way contamination. The design being simple, it is easy to incorporate it in conventional popular bandages at a minimal additional cost and has the same ease of handling as the conventional popular adhesive bandages. Further, grasping the tear away tabs in an equidistant manner from the central protective pad gives the applicant precise control, obviating misapplication. The uneven margins of the ends of the envelope provide ease of grasping, separating and opening the two leaves or the sheets of the encasing envelope.

Here one wishes to reiterate that the foregoing descriptions and examples and dimensions have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims and equivalents thereof.

I claim:

1. A bandage comprising:
   a support including a first side and a second side, the support defining a center;
   an adhesive portion over the first side of the support;
   a first section over the first side of the support, the first section including
      a first-section first layer, the first-section first layer including a distal part and a proximal part, the distal part of the first-section first layer being closer to the center than the proximal part of the first-section first layer, and a first-section second layer over the first-section first layer, the first-section second layer including a distal part and a proximal part, the proximal part of the first-section second layer being coupled to the proximal part of the first-section first layer, wherein the first-section layers are configured such that, when an applicant of the bandage pulls the distal part of the first-section second layer, the proximal part of the first-section second layer remains coupled to the proximal part of the first-section first layer whereby the first section separates from the support, and the distal part of the first-section second layer separates from the distal part of the first-section first layer such that the first-section first layer is between the applicant and the adhesive portion thereby acting to isolate fingers and hand of the applicant from the adhesive portion; and a second section over the first side of the support, the second section including a second-section first layer, the second-section first layer including a distal part and a proximal part, the distal part of the second-section first layer being closer to the center than the proximal part of the second-section first layer, and a second-section second layer over the second-section first layer, the second-section second layer including a distal part and a proximal part, the proximal part of the second-section second layer being coupled to the proximal part of the second-section first layer, wherein the second-section layers are configured such that, when the applicant of the bandage pulls the distal part of the second-section second layer, the proximal part of the second-section second layer remains coupled to the proximal part of the second-section first layer whereby the second section separates from the support, and the distal part of the second-section second layer separates from the distal part of the second-section first layer such that the second-section first layer is between the applicant and the adhesive portion thereby acting to isolate finger/s and hand of the applicant from the adhesive portion.

2. A bandage according to claim 1 wherein the center portion covered by the distal part of the first section first layer does not have the adhesive portion.

3. A bandage comprising:
a support including a first side and a second side;
a sterile pad over the first side of the support, the sterile pad defining a major surface;
which comes in contact with the wound and/or the surface of the receptor to be covered;
an adhesive portion over the first side of the support;
a first section over the sterile pad and the adhesive portion, the first section including
a first layer over the sterile pad, the first layer including a distal part and a proximal part, and
a second layer over the first layer, the second layer including a distal part and a proximal part, the proximal part of the second layer being coupled to the proximal part of the first layer, wherein the layers are configured such that, when an applicant of the bandage pulls the distal part of the second layer, the proximal part of the second layer remains coupled to the proximal part of the first layer whereby the first section separates from the support, and the distal part of the second layer separates from the distal part of the first layer such that the first layer is between the applicant and the sterile pad thereby acting to isolate finger/s and hand of the applicant from the sterile pad; and a second section over the sterile pad and the adhesive portion, the second section being configured such that, when the applicant pulls the second section, the second section separates from the support, whereby the first and second sections separating from the support enables the major surface of the sterile pad to contact a wound and the skin surface of a receptor of the bandage.

4. A bandage according to claim 3 wherein the first layer completely covers the sterile pad.

5. A bandage according to claim 3 wherein the second layer is folded back on itself such that a part of the second layer is over another part of the second layer.

6. A bandage according to claim 3 wherein the first layer is of a first color and the second layer is of a color different from the first color.

7. A bandage according to claim 3 wherein the second section includes
a first layer over the sterile pad and the adhesive portion, the first layer including a distal part and a proximal part, and the distal part covering the sterile pad and/or the distal part of first section first layer
a second layer over the first layer, the second layer including a distal part and a proximal part, the proximal part of the second layer being coupled to the proximal part of the first layer,
wherein the layers of the second section are configured such that, when an applicant of the bandage pulls the distal part of the second layer of the second section, the proximal part of the second layer of the second section remains coupled to the proximal part of the first layer of the second section whereby the second section separates from the support, and the distal part of the second layer of the second section separates from the distal part of the first layer of the second section thereby acting to isolate finger/s of the applicant from the sterile pad.

8. A bandage according to claim 7 wherein the second layer of the second section is folded back on itself such that a part of the second layer of the second section is over another part of the second layer of the second section.

9. A bandage according to claim 7 wherein the first layer of the first section and the first layer of the second section are of a first color, and the second layer of the first section and the second layer of the second section are of a color different from the first color.

10. A bandage according to claim 3 wherein the support is perforated.

11. A assembly comprising:
a bandage according to claim 3; and
a sealed envelope including 2 leaves, the edges of the two leaves being unevenly cut to avoid creating an exact match between the 2 leaves, each leave having part of the surface uncovered by the other, to facilitate grasping and the ease of separation, wherein the bandage is inside the sealed envelope.

12. An assembly according to claim 11 wherein inner and outer surfaces of the 2 leaves of the envelope are of different colors to facilitate ease of identification.

13. A bandage according to claim 3 wherein the sterile pad defines a border, and the proximal part of the first layer is over the border.

* * * * *